US007846968B2

(12) United States Patent
Chien et al.

(10) Patent No.: US 7,846,968 B2
(45) Date of Patent: Dec. 7, 2010

(54) METHODS FOR QT INTERVAL CONTROL

(75) Inventors: Shuchean Chien, Skillman, NJ (US); Gerald Novak, Skillman, NJ (US); Luc Truyen, Pennington, NJ (US); Eric Yuen, Blue Bell, PA (US)

(73) Assignee: Janssen Pharmaceutica, N.V., Beerse (BE)

( * ) Notice: Subject to any disclaimer, the term of this patent is extended or adjusted under 35 U.S.C. 154(b) by 1054 days.

(21) Appl. No.: 11/329,757

(22) Filed: Jan. 11, 2006

(65) Prior Publication Data
US 2007/0010578 A1 Jan. 11, 2007

Related U.S. Application Data

(60) Provisional application No. 60/645,447, filed on Jan. 20, 2005.

(51) Int. Cl.
*A01N 47/10* (2006.01)
(52) U.S. Cl. ........................................ 514/489; 514/476
(58) Field of Classification Search ................. 514/183
See application file for complete search history.

(56) References Cited

U.S. PATENT DOCUMENTS

| 3,265,728 A | 8/1966 | Bossinger et al. |
| 3,313,692 A | 4/1967 | Bossinger et al. |
| 5,698,588 A | 12/1997 | Choi et al. |
| 5,854,283 A | 12/1998 | Choi et al. |
| 6,103,759 A | 8/2000 | Choi et al. |
| 2002/0107283 A1* | 8/2002 | Codd et al. ................. 514/489 |

FOREIGN PATENT DOCUMENTS

WO  WO 02/067923 A   9/2002

OTHER PUBLICATIONS

Singh, "Quinidine-Like Activity of a New Central Depressant 2-hydroxy-2-phenylethyl Carbamate (Styramate)", Archives Internationales De Pharmacodynamie Et De Therapie, 157(2):424-431 (1965) Coden: Aiptak; ISSN: 0003-9780, XP009065683.
Al-Muhammed, J., et al. "*In-Vivo* Studies on Dexamethasone Sodium Phosphate Liposomes", J. Microencapsulation (1996), vol. 13, No. 3, pp. 293-306.
Eyles, J., et al. "Oral Delivery and Fate of Poly(lactic acid) Microsphere-Encapsulated Interferon in Rats", J. Pharm. Pharmacology (1997) vol. 49, pp. 669-674.
Gao, Z-H, et al. "Controlled Release of a Contraceptive Steroid from Biodegradable and Injectable Gel Formulations: *In Vitro* Evaluation", Pharmaceutical Research, vol. 12, No. 6 (1995) pp. 857-863.
Minto, C., et al. "Pharmacokinetics and Pharmacodynamics of Nandrolone Esters in Oil Vehicle: Effects of Ester, Injection Site and Injection Volume", Journal of Pharmacology and Experimental Therapeutics, vol. 281, No. 1 (1997) pp. 93-102.
Ostro, M., et al. "Use of Liposomes as Injectable-Drug Delivery Systems", American Journal of Hospital Pharmacy, vol. 46 (1989) pp. 1576-1587.
Rao, K., "Recent Developments of Collagen-Based Materials for Medical Applications and Drug Delivery Systems", J. Biomaterial Sci. Polymer, vol. 7, No. 7 (1995) pp. 623-645.
Rohatagi, S., et al. "Pharmacokinetic and Pharmacodynamic Evaluation of Triamcinolone Acetonide After Intravenous, Oral, and Inhaled Administration", J. Clinical Pharmacology (1995) pp. 1187-1193.
Tjwa, M., "Budesonide Inhaled via Turbuhaler: A More Effective Treatment for Astha Than Beclomethasone Dipropionate via Roahaler", Annals of Allergy, Asthma, and Immunology, vol. 75 (1995) pp. 107-111.
Wilen, S., et al., "Strategies in Optical Resolutions", Tetrahedron Report No. 38, vol. 33, pp. 2725-2736.

* cited by examiner

*Primary Examiner*—James D Anderson
*Assistant Examiner*—Meghan Finn

(57) ABSTRACT

This invention is directed to methods for controlling the duration of the depolarization and repolarization of the cardiac ventricle and therefore the QT interval, in therapeutically useful ways in a subject, comprising administering to the subject in need thereof a therapeutically effective amount of a compound selected from the group consisting of Formula (I) and Formula (II), or a pharmaceutically acceptable salt or ester thereof:

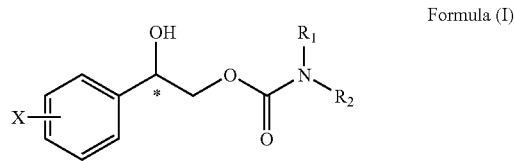

Formula (I)

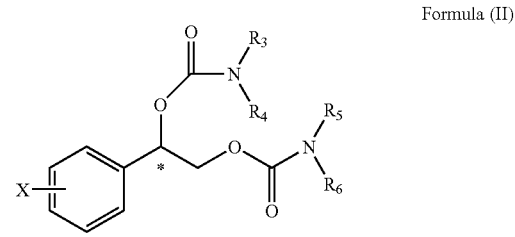

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$-$C_4$ alkyl; wherein $C_1$-$C_4$ alkyl is optionally substituted with phenyl, wherein phenyl is optionally substituted with substituents independently selected from the group consisting of halogen, $C_1$-$C_4$ alkyl, $C_1$-$C_4$ alkoxy, amino, nitro and cyano.

20 Claims, 1 Drawing Sheet

METHODS FOR QT INTERVAL CONTROL

CROSS REFERENCE TO RELATED APPLICATIONS

This application claims the benefit of U.S. Provisional application Ser. No. 60/645,447 filed Jan. 20, 2005. This Provisional application is hereby incorporated by reference.

BACKGROUND OF THE INVENTION

1. Field of the Invention

This invention relates generally to the fields of pharmacology and cardiology. In particular, the present invention provides methods for altering the rate of depolarization and repolarization of the ventricles of the heart. More specifically, this invention provides methods for the use of certain carbamate compounds to therapeutically alter the QT interval.

2. Description of the Related Art

The beating of the heart is a precisely controlled event that relies on the exact coordination of the atrial and ventricular contractions to obtain maximum pumping efficiency. The regularly spaced waves of myocardial excitation and contraction originate in the SA node and spread throughout the heart in well-defined manner. The electrocardiogram (ECG or EKG) provides valuable information about functional state and health and reflects the summation of all of the electrical activity in the heart. Electrical leads are placed on the body in specific places and the electrical activity resulting from heart depolarization, and repolarization, is recorded by each lead.

The size and direction of the ECG depends upon the direction that the electrical current is flowing, and on the magnitude of the muscle that is depolarized. Therefore, when the atria depolarize (and contract) the wave is smaller compared to when the ventricles contract. This is because the mass of atria are so much smaller then the ventricles. The repolarization of the ventricles (the T-wave) is in the same direction (positive) as the ventricular depolarization. This is because the ventricles depolarize from the inside to the outside (endocardium to epicardium), while repolarization occurs from the outside to the inside (epicardium to endocardium).

P-Wave: The cardiac cycle begins with the spontaneously firing cells in the SA node reaching threshold and generating action potentials. This produces a wave of depolarization that spreads to the left and downward though the atrial mass. The atria that were hyperpolarized suddenly become depolarized and the ECG records a positive deflection.

When the entire atria becomes depolarized the wave returns to 0. Then there is a delay of about 0.1 seconds, while the electrical current is passing through the AV node. When the AV node is depolarized it triggers depolarization of the Purkinje fibers. This tissue spreads the electrical current throughout the ventricles so that depolarization occurs across the entire ventricle simultaneously.

Next the ventricles depolarize resulting in the QRS complex. The 3 peaks are due to the way that current spreads through the ventricles, from inside to outside and because the tissue mass is greater on the left side then the right side. When the ventricles are completely depolarized the ORS complex is finished.

T-Wave: Repolarization of the ventricle leads to the T wave. Although the ventricles are repolarizing the T wave is still positive. This is because the heart repolarizes from outside to inside, the opposite direction of depolarization (it was inside to outside). This is the end of the cardiac cycle.

The QT interval is the time between the beginning of the QRS complex and the end of the T wave. This interval represents the time required for the depolarization and repolarization of the ventricle. The duration of the depolarization and repolarization of the ventricle can be affected by many conditions including; genetic variation, cardiac disease, electrolyte balance and many otherwise useful drugs. In many cases, prolongation of the QT interval beyond a certain point, by any of these conditions, can result in a dangerous situation in which the ventricle is at risk for possibly fatal arrhythmias. Thus, methods to control the duration of the QT interval and especially to shorten it, are needed.

SUMMARY OF THE INVENTION

This invention relates, in part, to methods and compounds useful for the controlling the duration of the depolarization and repolarization of the ventricle and therefore the OT interval, in therapeutically useful ways Accordingly, the present invention provides methods for altering, in a therapeutically useful manner, the QT interval of a subject in need thereof comprising administering to the subject a prophylactically or therapeutically effective amount of a composition that comprises at least one compound of Formula 1 or Formula 2:

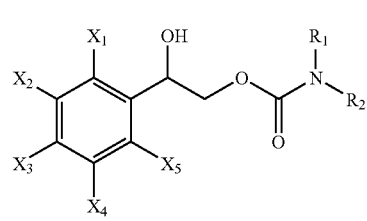

Formula 1

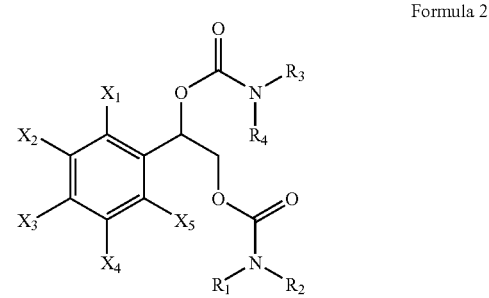

Formula 2 or a pharmaceutically acceptable salt or ester form thereof, wherein $R_1$, $R_2$, $R_3$ and $R_4$ are independently hydrogen or $C_1$-$C_4$ alkyl, wherein said $C_1$-$C_4$ alkyl is substituted or unsubstituted with phenyl, and wherein said phenyl is substituted or unsubstituted with up to five substituents independently selected from halogen, $C_1$-$C_4$ alkyl, $C_1$-$C_4$ alkoxy, amino wherein amino is optionally mono or disubstituted with $C_1$-$C_4$ alkyl, nitro or cyano; and $X_1$, $X_2$, $X_3$, $X_4$ and $X_5$ are independently hydrogen, fluorine, chlorine, bromine or iodine. Embodiments of the present invention include a compound of Formula 1 or Formula 2 wherein $X_1$, $X_2$, $X_3$, $X_4$ and $X_5$ are independently selected from hydrogen, fluorine, chlorine, bromine or iodine.

In certain embodiments, $X_1$, $X_2$, $X_3$, $X_4$ and $X_5$ are independently selected from hydrogen or chlorine. In other embodiments, $X_1$ is selected from fluorine, chlorine, bromine or iodine. In another embodiment, $X_1$ is chlorine, and $X_2$, $X_3$, $X_4$ and $X_5$ are hydrogen.

In another embodiment, $R_1$, $R_2$, $R_3$ and $R_4$ are hydrogen.

The present invention provides enantiomers of Formula 1 or Formula 2 for controlling the duration of the depolarization and repolarization of the ventricle and therefore the QT interval, in therapeutically useful ways, in a subject in need thereof. In certain embodiments, a compound of Formula 1 or Formula 2 will be in the form of a single enantiomer thereof. In other embodiments, a compound of Formula 1 or Formula 2 will be in the form of an enantiomeric mixture in which one enantiomer predominates with respect to another enantiomer.

In another aspect, one enantiomer predominates in a range of from about 90% or greater. In a further aspect, one enantiomer predominates in a range of from about 98% or greater.

The present invention also provides methods comprising administering to the subject a prophylactically or therapeutically effective amount of a composition that comprises at least one compound of Formula 1 or Formula 2 wherein $R_1$, $R_2$, $R_3$ and $R_4$ are independently selected from hydrogen or $C_1$-$C_4$ alkyl; and $X_1$, $X_2$, $X_3$, $X_4$ and $X_5$ are independently selected from hydrogen, fluorine, chlorine, bromine or iodine.

In embodiments of the present invention, the administration of one or more compounds of Formula 1 or formula 2 will occur before, after or simultaneously with the administration of one or more therapeutic agents. These therapeutic agents include other compounds that can by themselves shorten the QT interval and may work in an additive or synergistic fashion with the compounds of the invention and may also include therapeutic agents that have as a adverse side effect the unwanted property of prolonging the subjects QT interval in an undesirable or even dangerous manner.

The present invention provides methods comprising prophylactically or therapeutically administering to the subject a composition that comprises at least one compound having Formula 1 or Formula 2.

In certain embodiments of the present invention, a prophylactically or therapeutically effective amount of a compound of Formula 1 or Formula 2 for controlling the duration of the depolarization and repolarization of the ventricle and therefore the QT interval, in therapeutically useful ways is in a range of from about 0.01 mg/Kg/dose to about 150 mg/Kg/dose.

In certain embodiments, a prophylactically or therapeutically effective amount of a pharmaceutical composition for altering a subjects QT interval comprising one or more of the enantiomers of a compound of Formula 1 or Formula 2 includes a pharmaceutically acceptable salt or ester thereof in admixture with a pharmaceutically acceptable carrier or excipient, whereby such a composition is administered to the subject in need of treatment. Pharmaceutical compositions comprising at least one compound having Formula 1 or Formula 2 and one or more pharmaceutically acceptably excipients are administered to a subject in need thereof.

In certain embodiments, a subject or patient in need of treatment will not have a abnormal QT interval prior to administration of a compound of the invention and may be a subject or patient determined to be at risk for developing an abnormal QT interval because of the planned administration of a drug know to prolong the QT interval or because of an electrolyte abnormality or cardiac disease. In some embodiments the subject or patient in need of treatment may have a OT or QTc interval within the normal limits but may be at risk for a ventricular arrhythmia because of a known genetic predisposition or because of a personal or family history and/or a validated biomarker suggesting such a risk, due to known or unknown causes.

In another aspect, the subject or patient will be determined to be at risk for developing a dangerously prolonged QT interval on the basis of an ECG or other electrophysiological test at the time of administration.

DETAILED DESCRIPTION OF THE INVENTION

Figure 1:
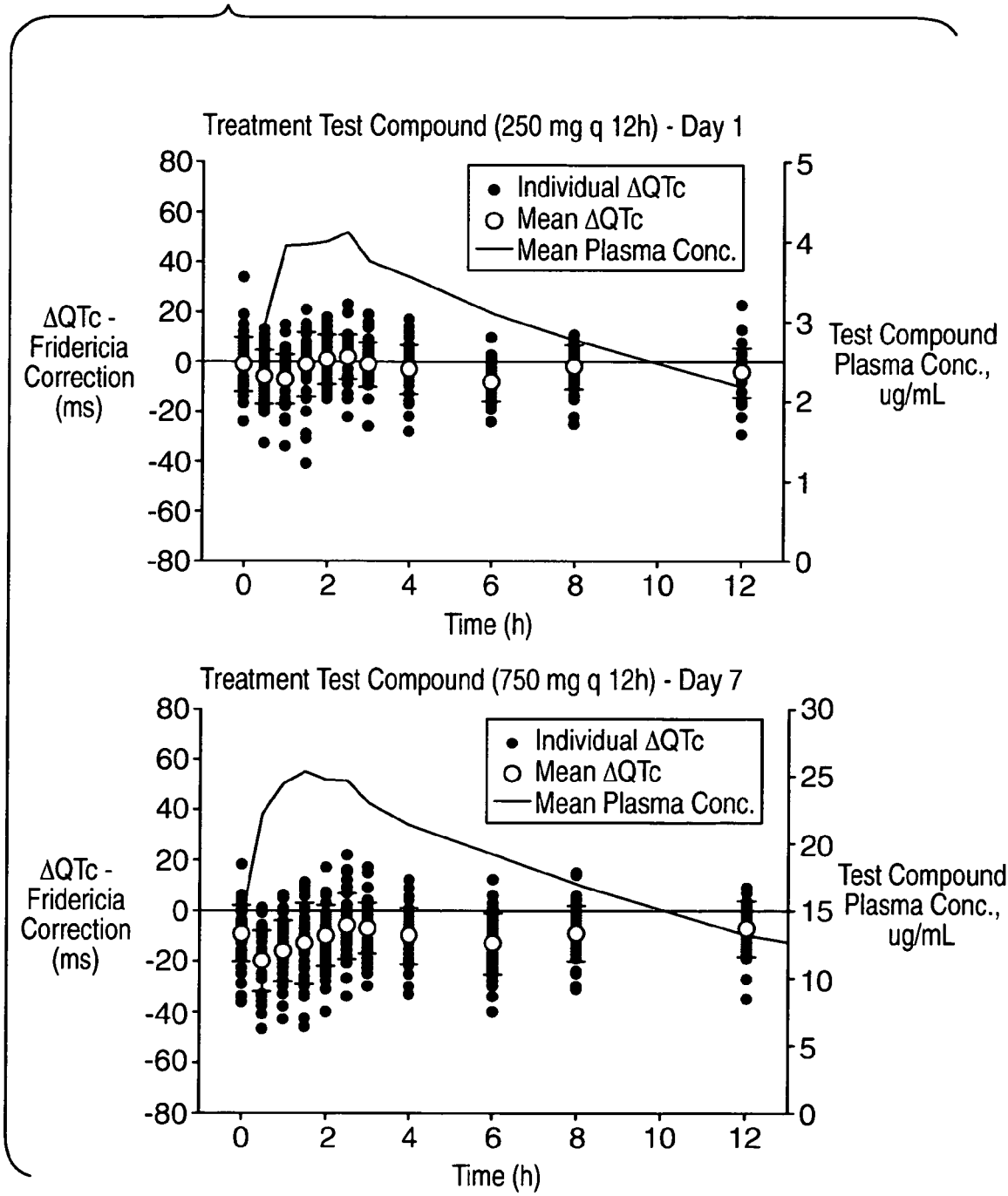
FIG. 1. Change From Baseline in QTc and Plasma Concentration Over Time in Subjects Treated with test compound.

This invention is based in part on the discovery that certain carbamate compounds, that also have utility as anti epileptic drug (AEDs) or anticonvulsants also shorten the QTc interval in human subjects. The precise mechanism of action is not clear however the compounds of this invention have unexpectedly been found to decrease the duration of the depolarization and repolarization of the ventricle and therefore the QT interval, in therapeutically useful ways.

Other well known drugs also shorten QT interval. These drugs include lidocaine, a sodium channel blocker, a local anesthetic and a Class 1b antiarrythmic agent, and phenyloin an antiepileptic drug (AED) that is also a Class 1b type antiarrythmic and has been used to treat ventricular tachyarrythmias induce by digitalis and polymorphic ventricular tachycardia associated with increased QT interval, i.e., Torsade de point (TdP)

This pharmacological property allows the compounds of the invention to be therapeutically useful in a variety of situations where a prolongation of the QT interval to an abnormal or possibly dangerous degree is a problem. This includes situations where the QT interval is lengthened either acutely or chronically. In addition, this includes conditions in which the QT or QTc is lengthened based on genetic factors i.e. the Long QT Syndrome, or where QT lengthening is due to the effect of drugs or pathological conditions of the heart including, but not limited to, cardiac ischemia and resulting myocardial damage.

Thus one aspect of this invention provides methods for correcting QT prolongation in subject due to genetic or congenital causes comprising administering a therapeutically effective dose of one of the compounds of the invention either alone or in combination with another therapeutically useful compound. Such genetic or congenital causes of a prolonged QT interval in a subject include, but are not limited to, Long QT Syndrome.

Other aspects of the present invention are methods to shorten or normalize the QT interval in a patient being administered another drug that can produce a prolongation of QT interval. The methods comprise administration of a therapeutically effective dose of one or more of the compounds of the invention to a subject whose QT interval would otherwise be abnormally prolonged due to another drug or therapeutic agent. The administration could occur either before or after the administration of the QT prolonging drug or the two or more drugs could be administered simultaneously, either separately or in a combined fixed dose format.

Still other aspects of this invention are methods to normalize or reduce the duration of the QT interval in subjects with acquired long QT that is due to pathological conditions including but not limited to; hypokalemia, hypomagnesemia, a liquid protein diet, starvation, central nervous disease and cardiac disease. These methods comprise administering to a subject with acquired long QT syndrome a therapeutically effective dosage or one or more of the compounds of the present invention alone or in combination with another therapeutically effective drug.

Definitions

As used herein the term "QT interval" shall mean the time required for depolarization and repolarization to occur in the cardiac ventricle. This is measured on the ECG as the time interval between the Q wave (the initial part of the QRS complex) and the end of the T wave.

As used herein, the term "QTc" (corrected QT interval) shall mean the measured QT interval corrected for heart rate by means of one of several possible algorithms. One formula is the one postulated by Bazett in 1920, this is calculated as QTc (Bazett)=QT/RR1/2, where RR1/2 is the square root of the heart rate in beats per minute. Another formula is the Friderica formula calculated as QTc (Friderica)=QT/RR1/3 where RR1/3 is the cube root of the heart rate in beats per minute. The third formula is the Individual Correction Method in which the post-dose of test medication QTc values are determined using the formula QTc=QT+bi(1-RR), where bi is the estimated slope for each individual subject via the linear regression models QT=α+βRR determined from the data collected from pretreatment baseline on day 0 of a medication trial and from the placebo treatment.

As used herein the term "prolonged QTc" shall mean a QTc (Friderica) of greater than 440 milliseconds in males and greater than 460 in females. Normal QTc in adult males is less than 430 milliseconds, borderline is 431-450 milliseconds and over 500 milliseconds is of clear concern, in adult females normal QTc is less than 450 milliseconds, borderline is 451-470 milliseconds and over 500 milliseconds is of clear concern.

As used herein, the term "Long QT Syndrome" means the congenital long QT syndromes including the Jervell and Lange-Nielsen syndromes, autosomal recessive and associated with congenital sensorineural deafness, and the Romano-Ward syndrome, autosomal dominant and associated with normal hearing, and other congenital long QT syndromes. Genetic abnormalities responsible for the Romano-Ward syndrome include heterozygous mutations of the KVLQT1, BERG, and SCN5A genes on chromosomes 11, 7, and 3, respectively; a locus on chromosome 4 may also be involved. Both the KVLQTI and BERG genes code for potassium channels. Failure of these channels to activate normally prolongs the action potential duration and provokes early afterdepolarizations. The SCN5A gene codes for sodium channel subunits; failure of this channel to inactivate also prolongs the action potential duration. Heterozygous mutations in the KVLQTI gene result in the Romano-Ward syndrome, whereas homozygous mutations result in the Jervell and Lange-Nielsen syndrome. The corrected QT interval (QTc) in Long QT Syndrome is usually greater than 460 milliseconds in men and 470 milliseconds in women, although affected individuals may have QT intervals that fall within the normal range. The QT interval fails to shorten normally or may prolong with exercise. Patients with the long QT syndrome are at risk for Torsade de point (TdP), which may result in syncope or sudden cardiac death. Slow ventricular rates or ventricular pauses can precipitate TdP due to bradycardia-dependent prolongation of the QT interval; alternatively, in some forms of the long QT syndrome, catecholamine stimulation, such as fright or exertion, may facilitate acquired long QT syndrome (TdP).

As used herein the term "Torsade de Pointes (TdP)" means a fast polymorphic ventricular arrhythmia associated with syncope and sudden death.

As used herein the term "acquired long QT syndrome" shall mean a condition of prolonged QT interval not due to the genetic conditions discussed above and usually related to electrolyte abnormalities such as hypokalemia and hypomagnesemia, or be caused by a liquid protein diet, starvation, central nervous system disease, and bradyarrythmias or by medications such as; tricyclic antidepressants, phenothiazines, non-sedating antihistamines such as terfenadine and astemizole (whose levels may be elevated by drugs that inhibit hepatic metabolism such as ketoconazole), macrolide antibiotics such as erythromycin, pentamidine, probucol, cisapride, and Class IA and Class III antiarrythmic medications or other medications including but not limited to those listed in Table 1. Acquired long QT syndrome, regardless of the cause may predispose the subject to TdP.

As used herein the term "ventricular fibrillation (VF)" is a malignant arrhythmia characterized by disorganized electrical activity resulting in a failure of sequential cardiac contraction and the inability to maintain cardiac output. VF results in hypoxemia and eventually sudden cardiac death.

As used herein the term "ventricular flutter" is an extremely rapid, hemodynamically unstable ventricular tachycardia (VT) that typically progresses to VF.

The terms "subject" or "patient" are used herein interchangeably and as used herein mean any mammalian subject or patient to whom the compositions of the invention can be administered. The term mammals include human patients and non-human primates, as well as experimental animals such as rabbits, rats, and mice, and other animals.

As used herein, the term "a subject in need of treatment" would include any individual who has a prolonged QTc interval for any reason or who is at risk of developing a prolonged QTc because of the planned administration of a drug that is known to have this effect. in addition, the term "a subject in need of treatment" would also include any individual whose clinical condition or prognosis, i.e., likelihood of developing an abnormal cardiac rhythm, could benefit from treatment with the compounds of this invention.

The term "treating" or "treatment" as used herein, refers to actions that cause any indicia of success in the prevention or amelioration of a prolonged QT interval.

Thus the term "treatment" or "to treat" is intended to include any action that improves, prevents, reverses, arrests, or inhibits the pathological process of QT prolongation, as that term is defined and used herein. The treatment or amelioration of symptoms can be based on objective or subjective parameters; including the results of an EKG or other physical examination technique.

The term "therapeutic effect" as used herein, refers to the therapeutic alteration of the QT interval in a subject. This would include, but not be limited to, decreasing the duration of the QT interval in a subject who has a genetic or congenital form of Long QT Syndrome or a subject who has an acquired form of prolongation of their QT interval due to an unwanted side effect of medication use, or due to electrolyte or cardiac pathology.

The term "a therapeutically effective amount" as used herein means a sufficient amount of one or more of the compounds of the invention to produce a therapeutic effect, as defined above, in a subject or patient in need of such treatment. Such a therapeutically effect may be a normalization of the subjects QT interval or may be a therapeutically y useful shorting of a prolonged QT interval even if it does not return to the normal range.

In some embodiments the compounds of the present invention would be used for the manufacture of a medicament for the purpose of decreasing the duration of the depolarization and repolarization of the cardiac ventricle and therefore the QT interval, in a therapeutically useful manner.

In some embodiments of the present invention carbamate compounds suitable for use in the practice of this invention will be administered either singly or concomitantly with at least one or more other compounds or therapeutic agents, e.g., with other antiarrythmic drugs, or drugs that can alter QT interval. In these embodiments, the present invention provides methods to alter OT interval in a patient. The method includes the step of; administering to a patient in need of treatment, an effective amount of one of the carbamate compounds disclosed herein in combination with an effective amount of one or more other compounds or therapeutic agents that have the ability to alter QT interval or the ability to augment the QT altering effects of the compounds of the invention. The administration of these two or more compounds may be simultaneous or in series, i.e., "concomitant administration" or "combination administration".

As used herein, the term "concomitant administration" or "combination administration" of a compound, therapeutic agent or known drug with a compound of the present invention means administration of the drug and the one or more compounds at such time that both the known drug and the compound will have a therapeutic effect. In some cases this therapeutic effect will be synergistic and in other cases the effect of one of the compounds of the invention will be to oppose the unwanted/adverse QT interval lengthening effect of another therapeutic agent. Such concomitant administration can involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compounds of the present invention.

The said one or more other compounds or therapeutic agents may be selected from compounds that have one or more of the following properties; causing an increase in the duration of the QT interval in a subject, have been associated with causing cardiac arrhythmias in patients with Long QT Syndrome or in subjects with other form of cardiac disease or disorder. In addition, the said one or more other compounds or therapeutic agents may be any agent known to alter the QT interval in a subject.

Table 1 below list some agents known to cause QT prolongation and/or are know to increase the likelihood that subjects with genetic, congenital or acquired Long QT Syndrome will develop a cardiac arrhythmia such as Torsade de pointes or other ventricular arrhythmia.

Table 1

Agents that can cause QT Interval Prolongation (Generic and Brand Names)

Albuterol (Ventolin®, Proventil®), Alfuzosin (Uroxatral®), Amantadine (Symmetrel®), Amiodarone (Pacerone®), Amiodarone (Cordarone®), Amitriptyline (Elavil®), Amoxapine (Asendin®), Amphetamine/dextroamphetamine (Adderall®), Ampicillin (Omnipen®), Ampicillin (Principen®), Arsenic trioxide (Trisenox®), Atomoxetine (Strattera®), Azithromycin (Zithromax®), Bepridil (Vascor®), Chloral hydrate (Noctec®), Chloroquine (Arelan®), Chlorpromazine (Thorazine®), Ciprofloxacin (Cipro®), Cisapride (Propulsid®), Clarithromycin (Biaxine), Clomipramine (Anafranil®), Cocaine (Cocaine), Desipramine (Pertofrane®), Dextroamphetamine (Dexadrine®), Disopyramide (Norpace®), Dobutamine (Dobutrex®), Dofetilide (Tikosyn®), Dolasetron (Anzemet®), Domperidone (Motilium®), Dopamine (Intropine®), Doxepin (Sinequan®), Droperidol (Inapsine®), Ephedrine (Broncholate®), Ephedrine (Rynatuss®), Epinephrine (Bronkaid®), Epinephrine (Primatene®), Erythromycin (E.E.S.®), (Erythrocin®), Felbamate (Felbatrol®), Fenfluramine (Pondimin®), Flecainide (Tambocor®), Fluconazole (Diflucan®), Fluoxetine (Prozace, Sarafem®), Foscamet (Foscavir®), Fosphenyloin (Cerebyx®), Galantamine (Reminyl®), Gatifloxacin (Tequin®), Granisetron (Kytril®), Halofantrine (Halfan®), Haloperidol (Haldol®), Ibutilide (Corvert®), Imipramine (Norfranil®), Indapamide (Lozol®), Isoproterenol (Isupres®), Isoproterenol (Medihaler-Iso®), Isradipine (Dynacirc®), Itraconazole (Sporanox®), Ketoconazole (Nizoral®), Levalbuterol (Xopenex®), Levofloxacin (LevaquinLevomethadyl (Orlaam®), Lithium (Eskalith®), Lithium (Lithobid), Mesoridazine (Serentile®), Metaproterenol (Alupent®), Metaproterenol (Metaprel®), Methadone (Dolophine, Methadose®), Methylphenidate (Ritalin®, Concerta®), Mexiletine (Mexitil®), Midodrine (ProAmatine®), Moexipril/HCTZ (Uniretic®), Moxifloxacin (Avelox®), Nicardipine (Cardene®), Norepinephrine (Levophed®), Nortriptyline (Pamelor®), Octreotide (Sandostatin®), Ondansetron (Zofran®), Paroxetine (Paxil®), Pentamidine (NebuPent®), Pentamidine (Pentam®), Phentermine (Fastin®), Phentermine (Adipex®), Phenylephrine (Neosynephrine®), Phenylpropanolamine (Dexatrim®), Phenylpropanolamine (Acutrim®), Pimozide (Orap®), Procainamide (Pronestyl) Procainamide (Procan®), Protriptyline (Vivactil®), Pseudoephedrine (PediaCare®), Pseudoephedrine (Sudafed®), Quetiapine (Seroquel®), Quinidine (Quinaglute®), Quinidine (Cardioquin®), Risperidone (Risperdal®), Ritodrine (Yutopar®), Salmeterol (Serevent®), Sertraline (Zoloft®), Sibutramine (Meridia®), Sotalol (Betapace®), Sparfloxacin (Zagam®), Tacrolimus (Prograf®), Tamoxifen (Nolvadex®), Telithromycin (Ketek®), Terbutaline (Brethine®), Thioridazine (Mellaril®), Tizanidine (Zanaflex®), Trimethoprim-Sulfa (Sulfa®), Trimethoprim-Sulfa (Bactrim®), Trimipramine (Surmontil®), Vardenafil (Levitra®), Venlafaxine (Effexor®), Voriconazole (VFend®), Ziprasidone (Geodon®), The Carbamate Compounds of the Invention The present invention provides methods of using 2-phenyl-1,2-ethanediol monocarbomates and dicarbamates in the therapeutic control of QT interval in a subject in need of such treatment.

Suitable methods for synthesizing and purifying carbamate compounds, including carbamate enantiomers, used in the methods of the present invention are well known to those skilled in the art. For example, pure enantiomeric forms and enantiomeric mixtures of 2-phenyl-1,2-ethanediol monocarbomates and dicarbamates are described in U.S. Pat. Nos. 5,854,283, 5,698,588, and 6,103,759, the disclosures of which are herein incorporated by reference in their entirety.

Representative carbamate compounds according to the present invention include those having Formula 1 or Formula 2:

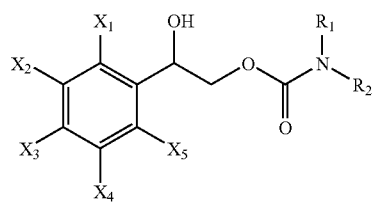

Formula 1

-continued

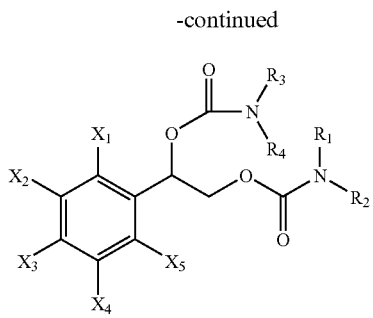

Formula 2 wherein $R_1$, $R_2$, $R_3$, and $R_4$ are, independently, hydrogen or $C_1$-$C_4$ alkyl and $X_1$, $X_2$, $X_3$, $X_4$, and $X_5$ are, independently, hydrogen, fluorine, chlorine, bromine or iodine.

"$C_1$-$C_4$ alkyl" as used herein refers to substituted or unsubstituted aliphatic hydrocarbons having from 1 to 4 carbon atoms. Specifically included within the definition of "alkyl" are those aliphatic hydrocarbons that are optionally substituted. In a preferred embodiment of the present invention, the $C_1$-$C_4$ alkyl is either unsubstituted or substituted with phenyl.

The term "phenyl", as used herein, whether used alone or as part of another group, is defined as a substituted or unsubstituted aromatic hydrocarbon ring group having 6 carbon atoms. Specifically included within the definition of "phenyl" are those phenyl groups that are optionally substituted. For example, in a preferred embodiment of the present invention, the, "phenyl" group is either unsubstituted or substituted with halogen, $C_1$-$C_4$ alkyl, $C_1$-$C_4$ alkoxy, amino, nitro, or cyano.

In a preferred embodiment of the present invention, $X_1$ is fluorine, chlorine, bromine or iodine and $X_2$, $X_3$, $X_4$, and $X_5$ are hydrogen.

In another preferred embodiment of the present invention, $X_1$, $X_2$, $X_3$, $X_4$, and $X_5$ are, independently, chlorine or hydrogen.

In another preferred embodiment of the present invention, $R_1$, $R_2$, $R_3$, and $R_4$ are all hydrogen.

It is understood that substituents and substitution patterns on the compounds of the present invention can be selected by one of ordinary skill in the art to provide compounds that are chemically stable and that can be readily synthesized by techniques known in the art as well as the methods provided herein.

Representative 2-phenyl-1,2-ethanediol monocarbomates and dicarbamates include, for example, the following compounds:

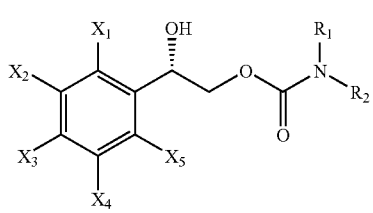

Formula 3

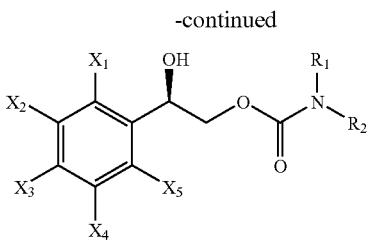

Formula 4

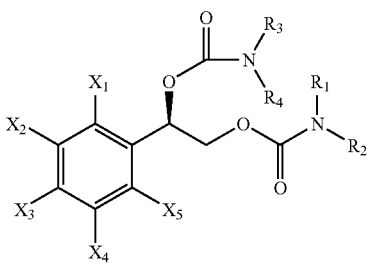

Formula 5

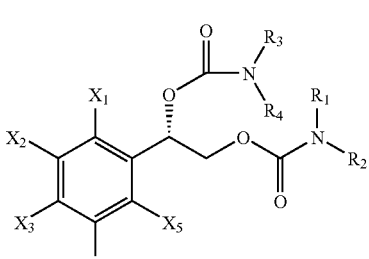

Formula 6

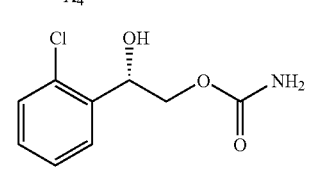

Formula 7

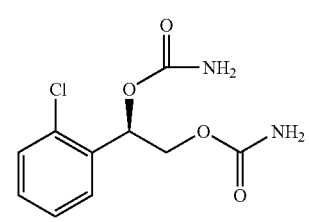

Formula 8

The present invention includes the use of isolated enantiomers of Formula 1 or Formula 2. In one preferred embodiment, a pharmaceutical composition comprising the isolated S-enantiomer of Formula 1 is used for controlling the duration of the depolarization and repolarization of the cardiac ventricle and therefore the QT interval, in therapeutically useful ways in a subject. In another preferred embodiment, a pharmaceutical composition comprising the isolated R-enantiomer of Formula 2 is used for controlling the duration of the depolarization and repolarization of the cardiac ventricle and therefore the QT interval, in therapeutically useful ways in a subject. In another embodiment, a pharmaceutical composition comprising the isolated S-enantiomer of Formula 1 and the isolated R-enantiomer of Formula 2 can be used for controlling the duration of the depolarization and repolarization of the cardiac ventricle and therefore the QT interval, in therapeutically useful ways in a subject.

The present invention also includes the use of mixtures of enantiomers of Formula 1 or Formula 2. In one aspect of the present invention, one enantiomer will predominate. An enantiomer that predominates in the mixture is one that is present in the mixture in an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1. In another preferred embodiment, the enantiomer that predominates in a composition comprising a compound of Formula 2 is the R-enantiomer of Formula 2.

In a preferred embodiment of the present invention, the enantiomer that is present as the sole enantiomer or as the predominate enantiomer in a composition of the present invention is represented by Formula 3 or Formula 5, wherein $X_1, X_2, X_3, X_4, X_5, R_1, R_2, R_3$, and $R_4$ are defined as above, or by Formula 7 or Formula 8.

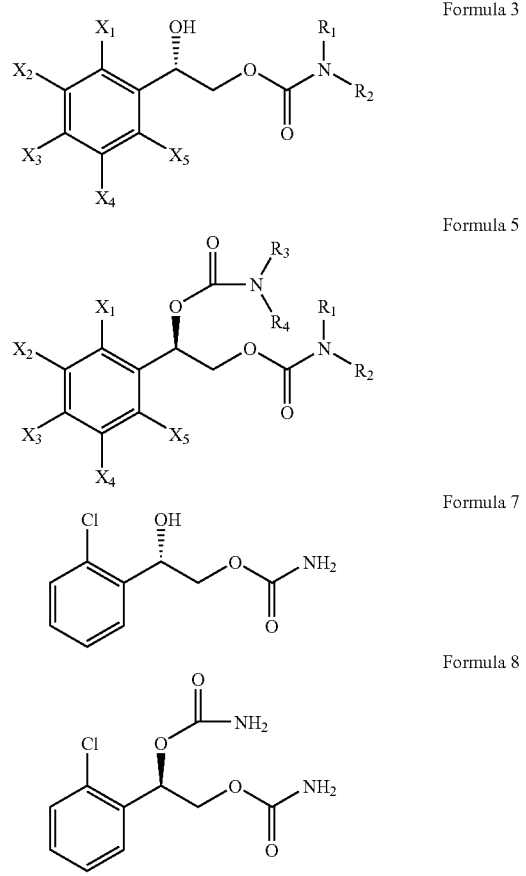

Formula 3

Formula 5

Formula 7

Formula 8

The present invention provides methods of using enantiomers and enantiomeric mixtures of compounds represented by Formula 1 and Formula 2 or a pharmaceutically acceptable salt or ester form thereof:

A carbamate enantiomer of Formula 1 or Formula 2 contains an asymmetric chiral carbon at the benzylic position, which is the aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer.

The term "substantially free," as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

Methods for the preparation of preferred enantiomers would be known to one of skill in the art and are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N.Y., 1962); and Wilen, S. H. Tables of Resolving Agents and Optical Resolutions p. 268 (E. L. Eliel, Ed., Univ. of Notre Dame Press, Notre Dame, Ind. 1972). Additionally, compounds of the present invention can be prepared as described in U.S. Pat. No. 3,265,728 (the disclosure of which is herein incorporated by reference in its entirety and for all purposes), U.S. Pat. No. 3,313,692 (the disclosure of which is herein incorporated by reference in its entirety and for all purposes), and the previously referenced U.S. Pat. Nos. 5,854,283, 5,698,588, and 6,103,759 (the disclosures of which are herein incorporated by reference in their entirety and for all purposes).

Carbamate Compounds as Pharmaceuticals

The present invention provides enantiomeric mixtures and isolated enantiomers of Formula 1 and/or Formula 2 as pharmaceuticals. The carbamate compounds are formulated as pharmaceuticals used for controlling the duration of the depolarization and repolarization of the cardiac ventricle and therefore the QT interval, in therapeutically useful ways in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 10% w of the carbamate compound, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropyl-methyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate.

Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and, as used herein, the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts and esters refer to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum.

Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arenesulfonic acids such as methanesulfonic acid and benzenesulfonic acid).

Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula 1 and Formula 2. More than one crystal form of an enantiomer of Formula 1 or Formula 2 can exist and as such are also included in the present invention.

A pharmaceutical composition of the invention can optionally contain, in addition to a carbamate compound, at least one other therapeutic agent useful in controlling the duration of the depolarization and repolarization of the cardiac ventricle and therefore the QT interval, in therapeutically useful ways in a subject.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods for controlling the duration of the depolarization and repolarization of the cardiac ventricle and therefore the QT interval, in therapeutically useful ways in a subject using carbamate compounds. The amount of the carbamate compound necessary for controlling the duration of the depolarization and repolarization of the cardiac ventricle and therefore the QT interval, in therapeutically useful ways in a subject is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able, without undue experimentation, having regard to that skill and this disclosure, to determine a therapeutically effective amount of a particular substituted carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

A treatment regimen with the compounds of the present invention can commence, for example, after a subject receives a drug or medication that prolongs the QT interval. In one embodiment, a subject that is being treated with a compound having QT prolongation effects, e.g., psychotropic drug, or a subject having a disease associated with a risk of developing prolonged QT, e.g., cardiac ischemia can commence a treatment regimen with a carbamate compound of the present invention.

In certain embodiments, the carbamate compound can be administered daily for a set period of time (week, month, year). An attendant physician will know how to determine that the carbamate compound has reached a therapeutically effective level, e.g., clinical exam of a patient, or by measuring drug levels in the blood or cerebro-spinal fluid.

In this context, a therapeutically effective dosage of the biologically active agent(s) can include repeated doses within a prolonged treatment regimen that will yield clinically significant results for controlling the duration of the depolarization and repolarization of the cardiac ventricle and therefore the QT interval, in therapeutically useful ways in a subject. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg. to about one gram or more, for single or multiple daily administration, according to the particular need of the patient. By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1/mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

After a pharmaceutical comprising a carbamate compound has been formulated in a suitable carrier, it can be placed in an appropriate container and labeled for control of or treatment of altered QT interval. Additionally, another pharmaceutical comprising at least one other therapeutic agent useful in the treatment of altered QT interval or another disorder or condition but said other therapeutic agent has, as an unwanted side effect, the prolongation of the QT interval can be placed in the container as well and labeled for treatment of the indicated disease. Such labeling can include, for example, instructions concerning the amount, frequency and method of administration of each pharmaceutical.

Cardiovascular Findings of a Compound of Formula 7

The study of the cardiovascular effects of a carbamate compound of the present invention, shown as Formula 7 above, and hereafter referred to as "the test compound" was a single-center, double-blind, randomized, 3-way crossover, placebo- and active-control study. The test compound was studied at a dose of 1,500 mg/day (750 mg twice daily) both after acute dosing (250 mg, Day 1) and at steady state (Day 7). The study also evaluated the delayed post-treatment effects on Days 8-10. Moxifloxacin (400 mg, single oral dose) was used as an active control for the evaluation of QT/QTc on both Days 1 and 7.

Of the 38 subjects enrolled, 35 completed all 3 treatment conditions (placebo, moxifloxacin, test compound). Two subjects withdrew electively after receiving the first 3 days of the last treatment period (1 in moxifloxacin and 1 in test compound), and the last one withdrew because of an adverse event (respiratory tract infection) after the first treatment period (placebo), and before receiving any other treatment. Thus, all 38 subjects completed placebo treatment, 36 subjects completed the test compound treatment (and an additional subject provided data for Days 0 and 1 on test compound), and 36 completed moxifloxacin treatment (and 1 provided data for Days 0 and 1 on moxifloxacin). All 38 subjects were included in the safety evaluation; all collected drug level measurements and all available ECG recordings were included in data analyses.

The pharmacokinetics of the test compound was linear and proportional after single- and multiple-dose administration. The systemic exposure of moxifloxacin was consistent between the 2 single 400 mg doses on Day 1 and Day 7.

The study population consisted of 38 healthy adults (20 men and 18 women), age 18 to 50 years, with normal 12-lead ECG (normal sinus rhythm, QTc and QRS intervals) and no history of cardiovascular disease. Of the 38 subjects enrolled, 35 completed all 3 treatment conditions (placebo, moxifloxacin, test compound). Two subjects withdrew electively after receiving the first 3 days of the last treatment period (1 in moxifloxacin and 1 in test compound), and the last one withdrew because of an adverse event (respiratory tract infection) after the first treatment period (placebo), and before receiving any.

The study population consisted of 38 healthy adults (20 men and 18 women), age 18 to 50 years, with normal 12-lead ECG (normal sinus rhythm, QTc and QRS intervals) and no history of cardiovascular disease. Of the 38 subjects enrolled, 35 completed all 3 treatment conditions (placebo, moxifloxacin, test compound). Two subjects withdrew electively after receiving the first 3 days of the last treatment period (1 in moxifloxacin and 1 in test compound), and the last one withdrew because of an adverse event (respiratory tract infection) after the first treatment period (placebo), and before receiving any other treatment. Thus, all 38 subjects completed placebo treatment, 36 subjects completed test compound treatment (and an additional subject provided data for Days 0 and 1 on test compound), and 36 completed moxifloxacin treatment (and 1 provided data for Days 0 and 1 on moxifloxacin). All 38 subjects were included in the safety evaluation; all collected drug level measurements and all available ECG recordings were included in data analyses.

During each treatment period, 11 12-lead ECGs were collected at the same time of the day on Day 0 (baseline), Day 1 (initial treatment), and Day 7 (steady-state treatment); 4 additional ECGs were collected at exactly 24, 36, 48, and 72 hours after the last dose of Day 7 (post-treatment).

All ECG recordings of the same subject were read by the same blinded cardiologist. The QT intervals, from the onset of the QRS complex to the end of the T wave, were determined by the method of overlapping medians. The key QTc variables used in the assessment are listed below. The change from baseline ($\Delta$QTc) was calculated using time-matched values. The following parameters were calculated for each subject and treatment by averaging over all time points during the 12-hour dosing interval.

| | |
|---|---|
| Max$\Delta$QTc | Maximum change from baseline in QTc interval |
| Mean$\Delta$QTc | Mean change from baseline in QTc interval |
| $t_{max,\Delta QTc}$ | Time of Max$\Delta$QTc |
| $\Delta$QTc, $t_{max}$ | Change from baseline in QTc interval at $t_{max}$ |

For both the initial (Day 1) and steady-state (Day 7) treatment effects, the mean $\Delta$QTc for test compound, placebo, and moxifloxacin are shown in Table 2 below, based on 3 different QT correction methods.

TABLE 2

Initial and Steady-State Treatment Effect on QTc Interval[1]:
Mean Change from Pretreatment Baseline
(Study test compound)

| | Day 1 (Acute Dosing) | | | Day 7 (Steady State) | | |
|---|---|---|---|---|---|---|
| Correction Method[2] | test compound N = 37 | Placebo N = 38 | Moxifloxacin N = 37 | test compound N = 36 | Placebo N = 38 | Moxifloxacin N = 36 |
| Fridericia | −3.1 (−12.6 to 4.9) p = 0.025* | −0.6 (−12.1 to 13.0) | +6.7 (−3.1 to 22.0) p < 0.001* | −11.2 (−27.6 to 1.8) p < 0.001* | +0.2 (−12.3 to 13.1) | +1.6 (−13.8 to 16.0) p = 0.382 |
| Bazett | −3.2 (−16.5 to 20.6) p = 0.346 | −1.9 (−11.9 to 18.6) | +6.5 (−7.7 to 27.3) p < 0.001* | −7.4 (−29.4 to 8.8) p < 0.001* | −0.5 (−13.4 to 18.0) | +3.2 (−17.3 to 28.9) p = 0.071 |
| Individual | −3.7 (−13.3 to 4.3) p = 0.002* | −0.1 (−8.7 to 11.0) | +6.6 (−2.9 to 20.6) p < 0.001* | −12.1 (−37.8 to 1.9) p < 0.001* | +0.1 (−11.3 to 11.1) | +0.8 (−12.6 to 15.5) p = 0.628 |

[1]Data are presented as mean (range). P-value as compared to placebo. All measurements are provided in ms. Statistically significant differences at the 0.05 level are denoted by an asterisk.
[2]QTc was calculated using 3 methods: the Bazett's square root formula, Fridericia's cubic root formula, and the Individual Correction Method (in which the post-dose QTc values were determined using the formula QTci = QTi + bi (1-RR), where bi is the estimated slope for each individual subject via the linear regression models QT = $\alpha$ + $\beta$RR determined from the data collected from pretreatment baseline on Day 0 and from the placebo treatment).

Compared to pretreatment baseline (Day 0), test compound reduced the mean QTc-F interval after initial treatment (Day 1) by 3.1 ms; and at steady state by 11.2 ms. Both changes were statistically significant. The active control (moxifloxacin at a single oral dose of 400 mg) increased QTc interval as expected. This increase was statistically significant compared to baseline only on Day 1, but not on Day 7.

There was no gender effect with regard to QTc reduction by test compound. The QTc shortening effect of test compound disappeared by 24 hours after the last dose of Day 7. There was no apparent delayed post-treatment effect on QT/QTc intervals on Days 8-10.

Initial and steady state treatment effects on QTc by Fridericia Correction Method (QTc-F) are shown in FIG. 1. QTc shortening at steady state (on Day 7), compared to baseline, was between 30 and 60 ms in 14 subjects treated with test compound, 1 placebo-treated subject, and 5 subjects receiving moxifloxacin. Of these, 2 subjects receiving test compound treatment and 1 subject receiving placebo had QTc-F slightly below 350 ms. The lowest QTc-F value, observed in 3 subjects, was 348 ms. The maximum decreases in QTc-F, compared to baseline, were 47 ms for test compound, 32 ms for placebo, and 45 ms for moxifloxacin.

Conclusion

Compared to pretreatment baseline (Day 0), test compound test compound statistically significantly reduced the mean QTc-F interval after initial treatment (Day 1) by 3.1 ms and at steady state (Day 7) by 11.2 ms. Based on the consistency of this effect across multiple time points and its disappearance by 24 hours post last dose, the shortening of QTc is judged to be an effect of test compound treatment.

References Cited

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description and accompanying drawings. Such modifications and variations are intended to fall within the scope of the appended claims. The present invention is to be limited only by the terms of the appended claims, along with the full scope of equivalents to which such claims are entitled.

What is claimed is:

1. A method for controlling the duration of the depolarization and repolarization of the cardiac ventricle and therefore shortening the QT interval, in a patient in need of treatment for a prolonged QTc inteval comprising administering to a patient with a prolonged QTc interval a therapeutically effective amount of a compound, or a pharmaceutically acceptable salt thereof, of a compound of Formula (I):

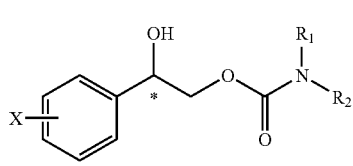

Formula (I)

wherein phenyl is ortho substituted at X with one chlorine atom; and $R_1$ and $R_2$, are hydrogen.

2. A method for controlling the duration of the depolarization and repolarization of the cardiac ventricle and therefore shortening the QT interval, in a patient in need of treatment for a prolonged QTc interval comprising, administering to a patient with a prolonged QTc interval, a therapeutically effective amount of an enantiomer, or a pharmaceutically acceptable salt thereof, of a compound of Formula (I) or enantiomeric mixture wherein one enantiomer selected from the group consisting of Formula (I) predominates:

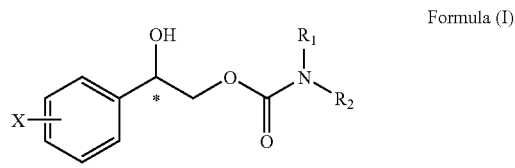

Formula (I)

wherein phenyl is ortho substituted at X with one chlorine atom and $R_1$ and $R_2$, are hydrogen.

3. The method of claim 2 wherein one enantiomer of Formula (I) predominates to the extent of about 90% or greater.

4. The method of claim 2 wherein one enantiomer of Formula (I) predominates to the extent of about 98% or greater.

5. The method of claim 2 wherein the enantiomer selected from the group consisting of Formula (I) is an enantiomer of Formula (Ia):

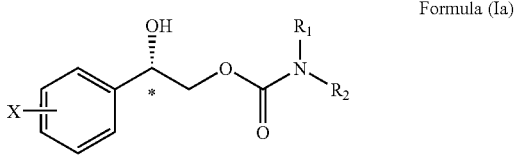

Formula (Ia)

wherein phenyl is ortho substituted at X with one chlorine atom and, $R_1$ and $R_2$ are hydrogen.

6. The method of claim 5 wherein one enantiomer of Formula (Ia) predominates to the extent of about 90% or greater.

7. The method of claim 5 wherein one enantiomer of Formula (Ia) predominates to the extent of about 98% or greater.

8. The method of claim 2 wherein the enantiomer selected from the group consisting of Formula (I) is an enantiomer of Formula (Ib) or a pharmaceutically acceptable salt thereof:

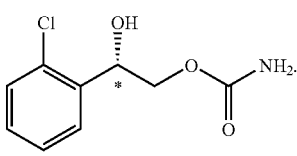

Formula (Ib)

9. The method of claim 8 wherein one enantiomer consisting of Formula (Ib) predominates to the extent of about 90% or greater.

10. The method of claim 8 wherein one enantiomer consisting of Formula (Ib) predominates to the extent of about 98% or greater.

11. The method, as claimed in claim 1 or 2 wherein has one or more factor(s) which the patient in need of treatment for a prolonged QTc interval are selected from the group consisting of: genetic predisposition, electrolyte abnormality, the effect of a QT prolonging drug and injury or trauma of any kind to the heart.

12. The method of claim 11 wherein the factor(s) rendering the patient in need of treatment is the effect of a QT prolonging drug.

13. The method of claim 12 wherein the said QT prolonging drug:
is selected from the group consisting of; Albuterol, Alfuzosin, Amantadine, Amiodarone, Amiodarone, Amitriptyline, Amoxapine, Amphetamine/dextroamphetamine, Ampicillin, Ampicillin, Arsenic trioxide, Atomoxetine, Azithromycin, Bepridil, Chloral hydrate, Chloroquine, Chlorpromazine, Ciprofloxacin, Cisapride Clarithromycin, Clomipramine, Cocaine, Desipramine, Dextroamphetamine, Disopyramide, Dobutamine, Dofetilide, Dolasetron, Domperidone, Dopamine, Doxepin, Droperidol, Ephedrine, Ephedrine, Epinephrine, Epinephrine, Erythromycin, Felbamate, Fenfluramine, Flecainide, Fluconazole, Fluoxetine, Foscarnet, Fosphenytoin, Galantamine, Gatifloxacin, Granisetron, Halofantrine, Haloperidol, Ibutilide, Imipramine, Indapamide, Isoproterenol, Isoproterenol, Isradipine, Itraconazole, Ketoconazole, Levalbuterol, Levofloxacin, Lithium, Mesoridazine, Metaproterenol, Metaproterenol, Methadone, Methylphenidate, Mexiletine, Midodrine, Moexipril/HCTZ, Moxifloxacin, Nicardipine, Norepinephrine, Nortriptyline, Octreotide, Ondansetron, Paroxetine, Pentamidine, Pentamidine, Phentermine, Phentermine, Phenylephrine, Phenylpropanolamine, Pimozide, Procainamide, Protriptyline, Pseudoephedrine, Pseudoephedrine, Quetiapine, Quinidine, Quinidine, Risperidone, Ritodrine, Salmeterol, Sertraline, Sibutramine, Sotalol, Sparfloxacin, Tacrolimus, Tamoxifen, Telithromycin, Terbutaline, Thioridazine, Tizanidine, Trimethoprim-Sulfa, Trimipramine, Vardenafil, Venlafaxine, Voriconazole and Ziprasidone.

14. The method of claim 11 wherein the said factor(s) rendering the patient in need of such treatment is a genetic predisposition to Long QT Syndrome.

15. The method of claim 14 wherein the factor(s) rendering the patient in need of such treatment is the presence of a prolonged QT interval in the subjects ECG.

16. The methods of claim 1 or 2 wherein said compound (or enantiomer) or a pharmaceutically acceptable salt thereof is administered in combination administration with one or more other compounds or therapeutic agents.

17. The methods of claim 16 wherein the said one or more other compounds or therapeutic agents are selected from the group consisting of; Albuterol, Alfuzosin, Amantadine, Amiodarone, Amiodarone, Amitriptyline, Amoxapine, Amphetamine/dextroamphetamine, Ampicillin, Ampicillin, Arsenic trioxide, Atomoxetine, Azithromycin, Bepridil, Chloral, hydrate, Chloroquine, Chlorpromazine, Ciprofloxacin, Cisapride, Clarithromycin, Clomipramine, Cocaine, Desipramine, Dextroamphetamine, Disopyramide, Dobutamine, Dofetilide, Dolasetron, Domperidone, Dopamine, Doxepin, Droperidol, Ephedrine, Ephedrine, Epinephrine, Epinephrine, Erythromycin, Felbamate, Fenfluramine, Flecainide, Fluconazole, Fluoxetine, Foscarnet, Fosphenytoin, Galantamine, Gatifloxacin, Granisetron, Halofantrine, Haloperidol, Ibutilide, Imipramine, Indapamide, Isoproterenol, Isoproterenol, Isradipine, Itraconazole, Ketoconazole, Levalbuterol, Levofloxacin, Lithium, Mesoridazine, Metaproterenol, Metaproterenol, Methadone, Methylphenidate, Mexiletine, Midodrine, Moexipril/HCTZ, Moxifloxacin, Nicardipine, Norepinephrine, Nortriptyline, Octreotide, Ondansetron, Paroxetine, Pentamidine, Pentamidine, Phentermine, Phentermine, Phenylephrine, Phenylpropanolamine, Phenylpropanolamine, Pimozide, Procainamide, Procainamide, Protriptyline, Pseudoephedrine, Pseudoephedrine, Quetiapine, Quinidine, Quinidine, Risperidone, Ritodrine, Salmeterol, Sertraline, Sibutramine, Sotalol, Sparfloxacin, Tacrolimus, Tamoxifen, Telithromycin, Terbutaline, Thioridazine, Tizanidine, Trimethoprim-Sulfa, Trimipramine, Vardenafil, Venlafaxine, Voriconazole and Ziprasidone.

18. The methods of claim 17 wherein the said one or more compounds are anti-arrhythmic drugs.

19. The method as in claim 1 or 2 wherein the therapeutically effective amount is from about 0.01 mg/Kg/dose to about 100 mg/Kg/dose.

20. The method, as claimed in claim 1 or 2, wherein said patient has developed a prolonged QT interval on ECG at the time of said administration.

* * * * *